US008747374B2

(12) United States Patent
Strandberg et al.

(10) Patent No.: US 8,747,374 B2

(45) Date of Patent: Jun. 10, 2014

(54) EMERGENCY EYEWASH UNIT

(71) Applicant: Haws Corporation, Sparks, NV (US)

(72) Inventors: Victor C. Strandberg, Washoe Valley, NV (US); Ian T. Roberts, Sparks, NV (US); Joshua D. Linn, Carson City, NV (US)

(73) Assignee: Haws Corporation, Sparks, NV (US)

( * ) Notice: Subject to any disclaimer, the term of this patent is extended or adjusted under 35 U.S.C. 154(b) by 0 days.

(21) Appl. No.: 14/062,779

(22) Filed: Oct. 24, 2013

(65) Prior Publication Data

US 2014/0047634 A1 Feb. 20, 2014

Related U.S. Application Data

(60) Division of application No. 13/660,820, filed on Oct. 25, 2012, now Pat. No. 8,566,974, which is a continuation of application No. 12/436,425, filed on May 6, 2009, now Pat. No. 8,316,478.

(60) Provisional application No. 61/054,626, filed on May 20, 2008.

(51) Int. Cl.
*A61M 35/00* (2006.01)

(52) U.S. Cl.
USPC ............ 604/294; 604/289; 604/290; 239/11; 239/16; 239/463; 239/472; 239/478; 4/620; 4/619; 4/615; 4/239; 4/568

(58) Field of Classification Search
USPC .......................................... 604/294, 289, 290
See application file for complete search history.

(56) References Cited

U.S. PATENT DOCUMENTS

| | | | | |
|---|---|---|---|---|
| 5,008,963 | A * | 4/1991 | Stein | 4/620 |
| 5,170,518 | A * | 12/1992 | Warriner | 4/620 |
| 5,754,990 | A * | 5/1998 | Gurries, II | 4/620 |
| 2005/0273924 | A1* | 12/2005 | Taylor | 4/620 |

* cited by examiner

*Primary Examiner* — Tatyana Zalukaeva
*Assistant Examiner* — Ilya Treyger
(74) *Attorney, Agent, or Firm* — Alston & Bird LLP

(57) ABSTRACT

An emergency eyewash unit includes a pair of water discharge ports oriented to produce a pair of upwardly directed, diverging water streams for inside-out flush flow of contaminants from a person's eyes. These eyewash streams can be combined with a plurality of smaller upwardly directed facewash streams for flushing contaminants from a person's face. The eyewash and/or facewash streams are produced by an eyewash body adapted for rotatable mounting onto a water supply conduit, with a locking clip normally preventing undesired rotational disassembly. The eyewash body may be used in combination with an overhead emergency shower which, in one preferred form, includes a shower spray head carrying multiple flow control and flow shaper elements to produce a substantially uniformly dispersed shower spray pattern.

20 Claims, 7 Drawing Sheets

EMERGENCY EYEWASH UNIT

CROSS-REFERENCE TO RELATED APPLICATIONS

This application is a divisional of and claims the benefit of priority to U.S. patent application Ser. No. 13/660,820, filed Oct. 25, 2012. U.S. patent application Ser. No. 13/660,820, in turn, is a continuation of and claims the benefit of priority to U.S. patent application Ser. No. 12/436,425 May 6, 2009, now U.S. Pat. No. 8,316,478. U.S. patent application Ser. No. 12/436,425, in turn, is a non-provisional of and claims the benefit of priority to U.S. Provisional Patent Application No. 61/054,626, filed May 20, 2008. The entire contents of all of the above-identified patent applications are expressly incorporated herein by reference.

BACKGROUND OF THE INVENTION

This invention relates generally to improvements in emergency eyewash stations designed particularly for use in a laboratory or industrial environment to provide a flush flow of water to remove irritants and/or contaminants from a person's eyes. More specifically, this invention relates to an improved emergency eyewash unit for providing an improved inside-out directed flush flow of water. In various preferred embodiments, the improved eyewash unit may additionally provide a facewash flush flow and/or an overhead emergency shower.

Emergency eyewash stations are generally known in the art for use in washing or flushing toxic substances from a person's eyes. Such eyewash stations are commonly used in laboratory and/or industrial applications wherein personnel are required to handle or otherwise work in proximity with substances which can be potentially harmful if contacted with the eyes. A typical eyewash station includes one or more spray nozzles or spray heads mounted over or in close association with an appropriate sink or drain, with means for rapidly and easily opening a valve to provide a flushing flow of water to a person's eyes and/or face to flush irritants and contaminants therefrom.

In the past, emergency eyewash stations have generally provided a pair of upwardly directed converging water streams for flushing contaminants from the eyes and face. See, for example, U.S. Pat. Nos. 5,740,469 and 5,754,990 which depict a pair of spray heads oriented to deliver a respective pair of water streams upwardly and angularly converging toward each other. However, such converging flush flow streams tend to wash contaminants located in or around a person's eyes in an outside-in, or inward, direction toward the person's tear ducts and sinus cavities. Accordingly, the inward-directed flush flows may carry the contaminants into contact with these anatomical structures where tissue damage can be increased. In addition, in the case of fluids washing into and around the nose, sinus cavities, and mouth, such fluids can be ingested and/or swallowed thereby further spreading the contaminants.

There exists, therefore, a significant need for improvements in and to eyewash stations, particularly with respect to providing improved water-flow flushing of contaminants from a person's eyes while reducing or eliminating contaminant contact with the person's tear ducts and/or sinus cavities. The present invention fulfills these needs and provides further related advantages.

SUMMARY OF THE INVENTION

In accordance with the invention, an improved emergency eyewash unit includes a pair of water discharge ports oriented to produce a pair of upwardly directed, diverging water streams for inside-out, or outwardly directed flush flow of contaminants from a person's eyes.

In a preferred form, the eyewash unit comprises an eyewash body adapted for connection to a water supply line or conduit. The eyewash body defines an upper discharge plate having a pair of diverging flow ports formed therein for upward projection therethrough of the pair of diverging eyewash flush flow water streams. These diverging flush flow streams are effective to wash or flush irritants and contaminants from a person's eyes in an inside-out direction, thereby flushing in a direction away from the person's tear ducts and sinus cavities.

In one alternative preferred form, the upper discharge plate may additionally include a plurality of small facewash perforations for upward flow of a corresponding plurality of relatively small facewash flush flow streams effective to flush irritants and contaminants from the person's face, in addition to the two diverging eyewash flush flow streams.

The eyewash body including the upper perforated discharge plate is adapted for quick and easy mounting as a unit with respect to a water supply line, preferably in a position generally within or centered over a drain basin. In the preferred form, an elbow or L-shaped strainer is coupled to a downstream end of the water supply line, and the eyewash body in turn includes a threaded fitting for threaded connection with the elbow fitting. A lock clip is removably attached to the eyewash body, as by means of a threaded fastener connecting the lock clip to a short flange on the eyewash body. The lock clip defines a forked leg structure having a pair of spaced-apart legs disposed on opposite sides of the water supply conduit. This pair of lock clip legs thus engage the water supply conduit to prevent rotational disassembly of the eyewash body from the associated L-strainer and water supply conduit, unless and until the lock clip is first disconnected from the eyewash body.

In a further alternative preferred form of the invention, the eyewash and/or combined eyewash/facewash unit may be additionally combined with an overhead emergency shower used to wash irritants and contaminants from a person's body. In the preferred form, the overhead shower comprises a spray head or spray nozzle adapted for installation at a downstream end of a water supply line or conduit to provide a downwardly directly shower spray aimed preferably to deluge a person using the eyewash or combined eyewash/facewash unit. The shower spray head may be adapted for thread-on mounting at the downstream end of the water supply line. A downwardly open shroud element is carried by the spray head generally in surrounding relation thereto. In the preferred form, the shroud element is rotatably mounted on the spray head but axially constrained by at least one snap ring to prevent rotational removal of the shroud element from the spray head.

A preferred shower head further comprises a nozzle body having a plurality of flow control and stream shaping components mounted therein, wherein this modified combination is designed to provide a regulated outflow of shower water which is substantially constant over a range of normal water inflow pressures, and further wherein the produced shower stream is relatively uniformly dispersed throughout a defined generally cone-shaped shower spray pattern to insure thorough rinsing of contaminants from a person using the shower. In this regard, the modified shower head combination is designed for substantially complete compliance with applicable safety codes and standards.

The preferred shower head includes a flexible pressure compensating flow control element for regulating the rate of water flow in response to a range of different upstream water supply pressures. This flow control element is mounted upstream from a flow control positioning or spacer washer designed to remove turbulence from the water flow stream. Water discharged from the spacer washer is directed into an axially elongated mixing chamber before encountering a diffuser disk which converts the water flow into a central stream and a spinning or swirling outer portion. The combined stream is directed through a short mixing chamber to a nozzle orifice which in turn supplies to the water via a exit cone for final shaping into a substantially uniformly dispersed conical shower spray pattern. A preferred exit cone geometry includes multiple conical segments defined by a progressively decreasing taper angle.

Other features and advantages of the present invention will become more apparent from the following detailed description taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
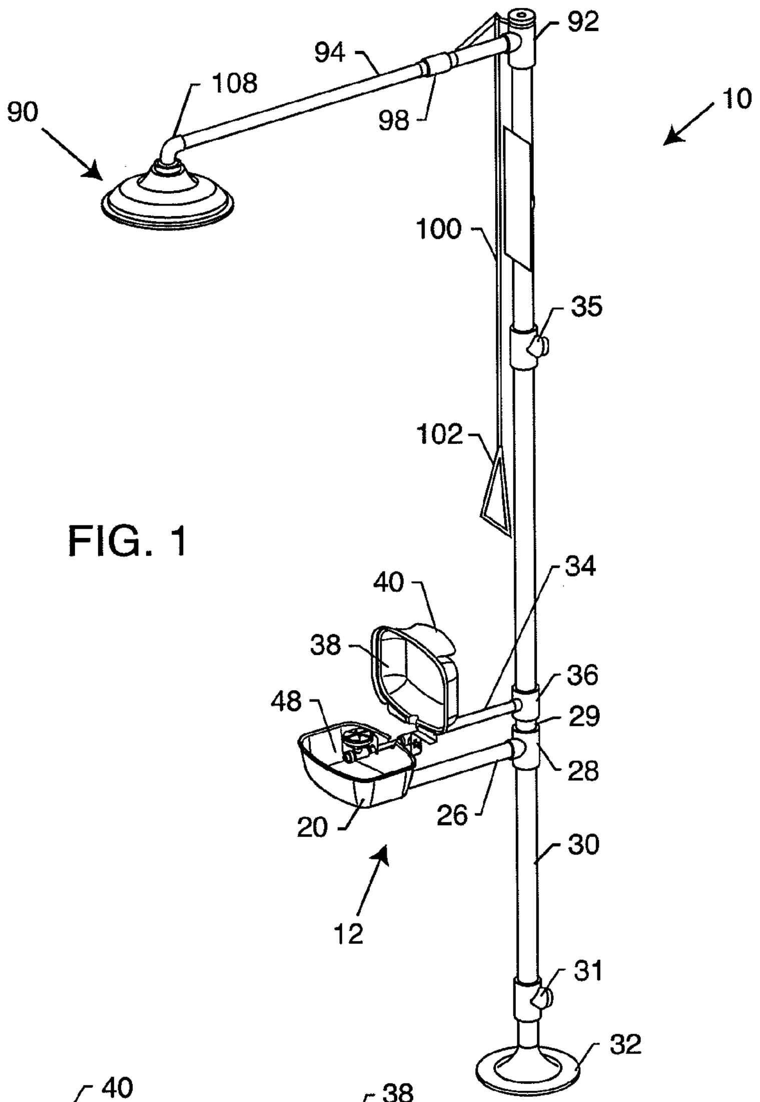
FIG. 1 is a perspective view of a combined emergency eyewash and emergency shower station, and depicting an emergency eyewash unit with a protective cover in an open position.
Figure 6:
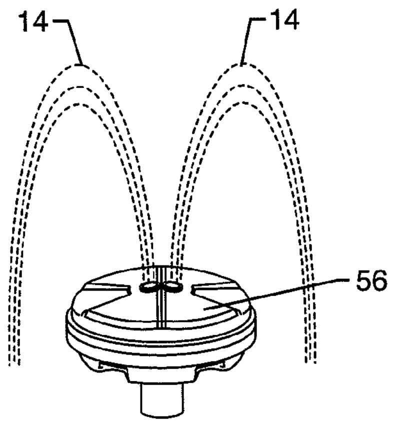
FIG. 6 is a simplified perspective view showing two angularly diverging water flush streams projected upwardly from the eyewash body of FIGS. 3-5.
Figure 7:
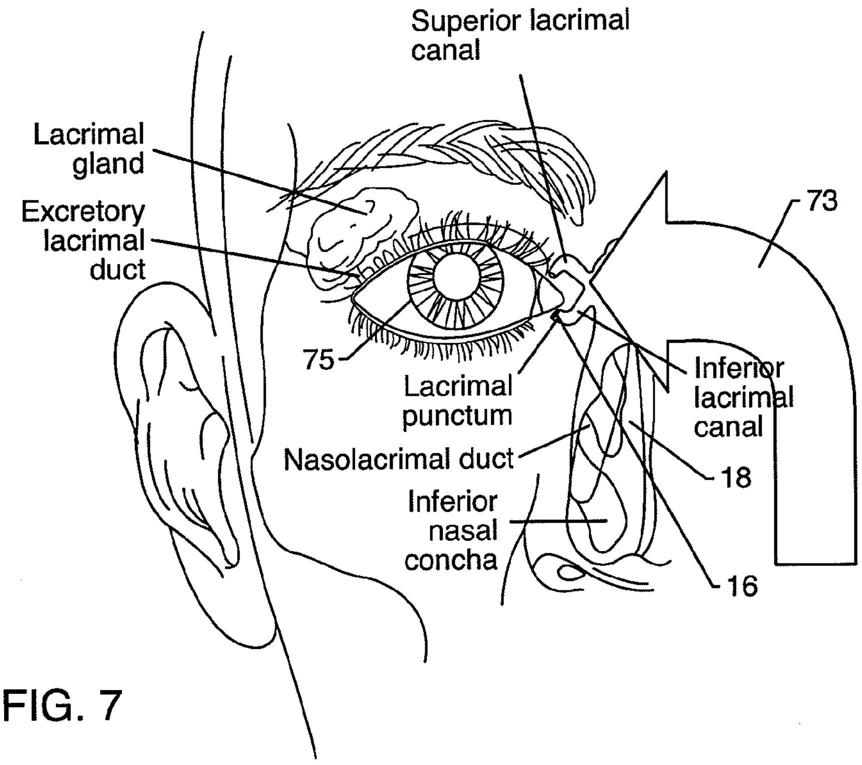
FIG. 7 is a diagrammatic view representing operation of the diverging water flush streams to flush contaminants from a person's eyes by water flow in an inside-out direction.

As shown in the exemplary drawings, an improved emergency wash station referred to generally in FIG. 1 by the reference numeral 10 has an eyewash unit 12 for flushing irritants and/or contaminants such as chemicals or other toxic substances from the eyes and/or face of an individual. The eyewash unit 12 includes means for producing a pair of upwardly directed eyewash flush flow streams 14 (FIG. 6) which diverge from each other and thereby function to flush contaminants in an inside-out, or outboard direction away from a person's tear ducts 16 and nasal or sinus cavities 18 (FIG. 7).

Figure 2:
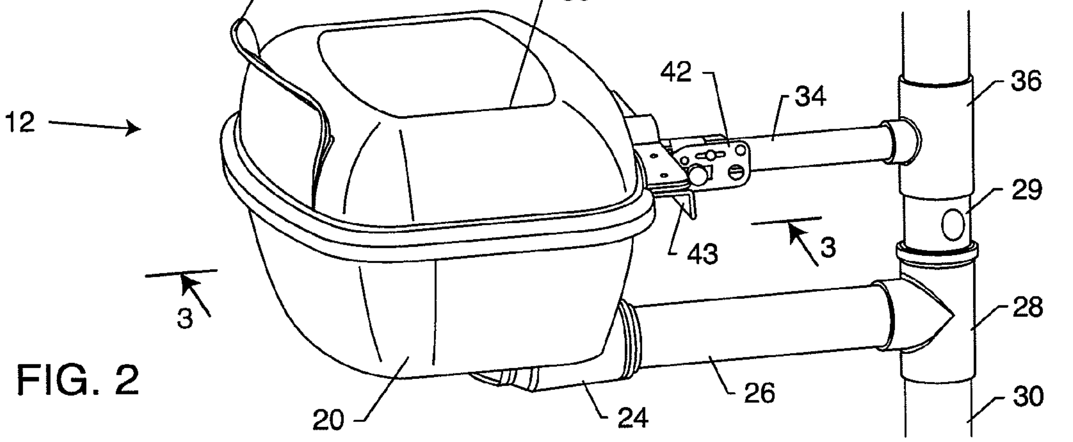
FIG. 2 is an enlarged and fragmented perspective view showing the emergency eyewash unit of FIG. 1 with the protective cover in a normal closed position.
Figure 3:
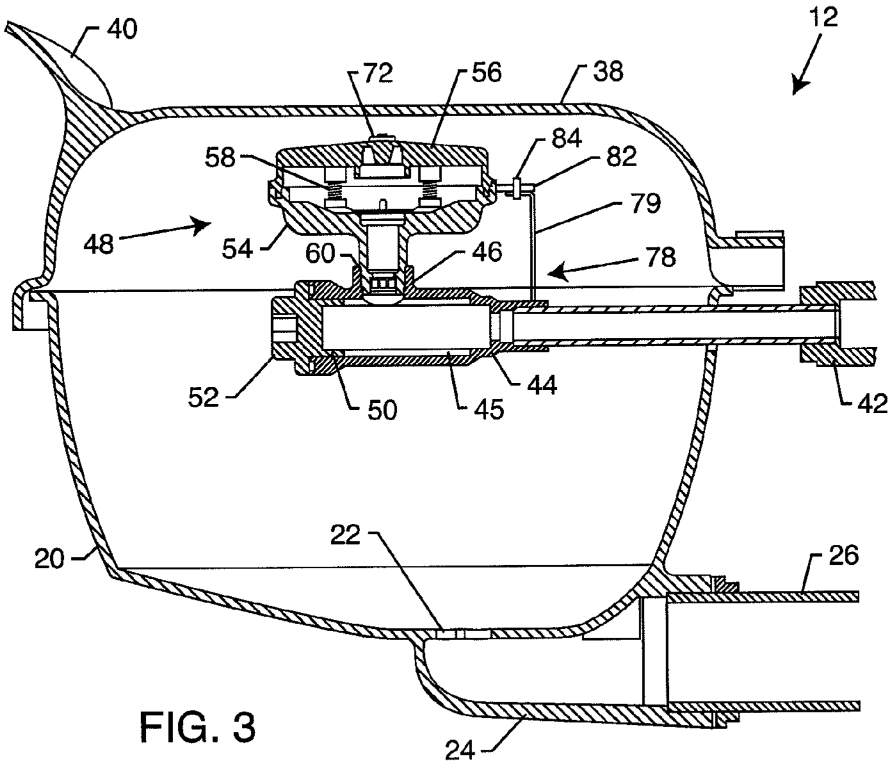
FIG. 3 is an enlarged vertical sectional view taken generally on the line 3-3 of FIG. 2, and illustrating an eyewash body coupled to a water supply line or conduit.

As shown in FIGS. 1-3, the eyewash unit 12 generally comprises a bowl-shaped basin 20 having an upwardly open geometry and defining an open lower drain port 22 (shown best in FIG. 3). The drain port 22 merges with a drain fitting 24 adapted for coupling with a drain line 26 having an opposite end connected with a tee fitting 28 (FIGS. 1 and 2) on an upright support stand 30. Although not shown in detail in the accompanying drawings, persons skilled in the art will appreciate that the support stand 30 has a hollow tubular construction forming a continuation of a drain path for water flow from the basin 20 to a suitable floor drain site (not shown) as via a lower tee fitting 31 (FIG. 1) disposed a short distance above an enlarged lower base 32 at the bottom of the support stand 30.

A water supply line or water supply conduit 34 extends from the support stand 30 for supplying water under pressure to the eyewash unit 12. More particularly, the water supply conduit 34 extends from a second tee fitting 36 on the support stand 30 spaced a short distance above the underlying drain line 26 and associated drain tee fitting 28, as by means of a plug member 29. This plug member 29 is preferably solid to preclude intermixing of the water supply and used or drain water, preferably to include a laterally open passage therein (shown best in FIG. 2) for clearing indicating separation of these water flows. An appropriate water supply source (not shown) for delivering water under pressure to the water supply line 34 is suitably coupled, e.g., via a supply tee 35 (FIG. 1) or the like coupled to the tee fitting 36 as by means of an upper segment of the support stand 30. If desired, this water source may include means for providing a tempered or warm water flow, such as shown and described in U.S. Pat. No. 5,350,112, which is incorporated by reference herein.

A downstream end of the water supply conduit 34 carries a pivotally mounted dust cover 38 movable between an open position (FIG. 1) exposing an eyewash body 48, and a closed position (FIGS. 2-3) overlying and concealing the eyewash body 48 within the basin 20. A handle or activation flag 40 located on the upper front of the cover 38 is easily grasped by the left or right hand for quick and easy displacement from the closed position to the open position, when emergency use of the eyewash unit 12 is desired or required. In this regard, the cover 38 is pivotally coupled to a valved connector 42 (FIGS. 3 and 10) on the water supply conduit 34 as by means of a hinge assembly 43 to actuate a valve (not shown) for initiating water flow to the eyewash unit 12, upon cover movement to the open position. Such valved operation for an emergency eyewash station is known in the art, e.g., as disclosed in U.S. Pat. No. 5,754,990 which is incorporated by reference herein.

An elbow or L-shaped strainer 44 (FIG. 3) is coupled as by means of a threaded connection with a downstream end of the valved pivotal connection 42 which is mounted in turn at a downstream end of the water supply conduit 34. Alternately, when an alternative on-off valve actuation means is used, the L-strainer 44 can be connected directly to the downstream end of the water supply conduit 34. As shown best in FIG. 3, this L-strainer extends into the lower basin 20, and defines an upwardly directed threaded fitting 46 for quick and easy removable mounting of the eyewash body 48 forming the eyewash unit 12. If desired, the L-strainer 44 may additionally include a cylindrical strainer screen 45 for straining particulate from the water supply stream prior to water flow upwardly through the threaded fitting 46 to the eyewash body 48. A horizontally open discharge port 50 is normally closed by a threaded plug 52 or the like, wherein this plug 52 can be removed as needed for easy access to and cleaning of the L-strainer interior and the strainer screen 45 contained therein, with flush flow of water during such cleaning passing through the discharge port 50 and into the basin 20 for drainage therefrom.

Figure 4:
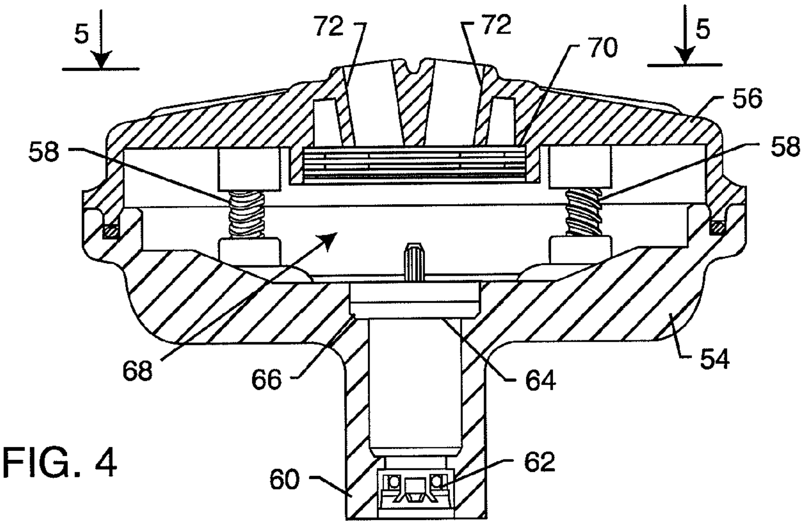
FIG. 4 is a further enlarged vertical sectional view showing internal construction details of the eyewash body of FIG. 3.
Figure 5:
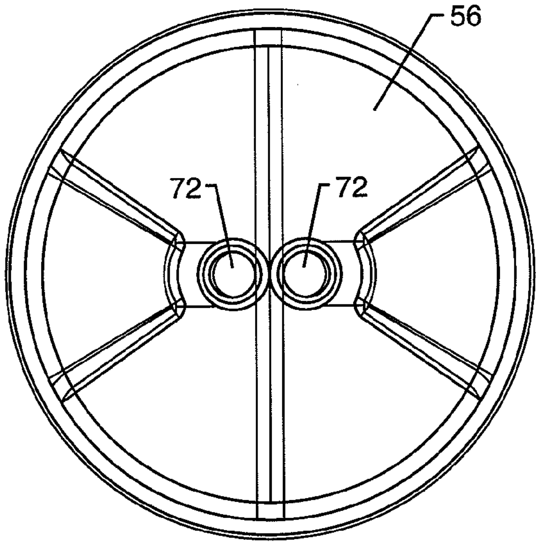
FIG. 5 is a top plan view of the eyewash body, taken generally on the line 5-5 of FIG. 4.

The eyewash body 48 comprises a relatively compact subassembly or module including a lower base member 54 having an upper discharge plate 56 attached thereto as by means of a pair of screws 58 (FIGS. 3-4). A lower central threaded fitting 60 depends from the underside of the base member 54 for quick and easy threaded attachment with the upper fitting 46 on the L-strainer 44. As shown, this lower fitting 60 carries flow control means such as a flow restrictor 62 for providing a substantially constant water inflow upwardly and through a laminar flow screen 64 retained in place by a washer 66, and into a central eyewash body chamber 68. From this central chamber 68, the water is permitted to flow further upwardly through a laminar flow means such as a laminar flow cartridge 70 containing multiple laminar flow screens, for upward discharge through a pair of discharge nozzles angularly diverging discharge ports 72 (FIGS. 3-5) formed in the discharge plate 56. Persons skilled in the art will recognize and appreciate that alternative flow control structures and alternative laminar flow structures can be used.

The pair of diverging discharge ports 72 provide the pair of upwardly directed and angularly diverging eyewash flush flow streams 14 (FIG. 6) to achieve the desired inside-out flush flow of contaminants from a person's face. These eyewash streams 14 are relatively solid, substantially laminar flow streams which arch upwardly for inside-out flush flow. As a person leans over these eyewash streams 14, the person's eyes are located substantially at the crests of the flush flows whereat substantial flow action with minimal kinetic energy and vertical velocity is provided. As viewed schematically in FIG. 7, such inside-out, or outboard directed flush flow generally in the direction of arrow 73, beneficially washes any irritants or contaminants on or near the eyes 75 in an outboard direction away from a person's tear ducts (lacrimal punctum) 16 and the adjacent nasal and sinus cavities 18. As a result, the contaminants are substantially prevented from contacting these tissue structures where they can otherwise be ingested to cause wider irritation and potential tissue damage. The flush flow water falls from the person's face downwardly into the open basin 20 for collection and further passage through the drain port 22 and drain conduit 24.

Figure 8:
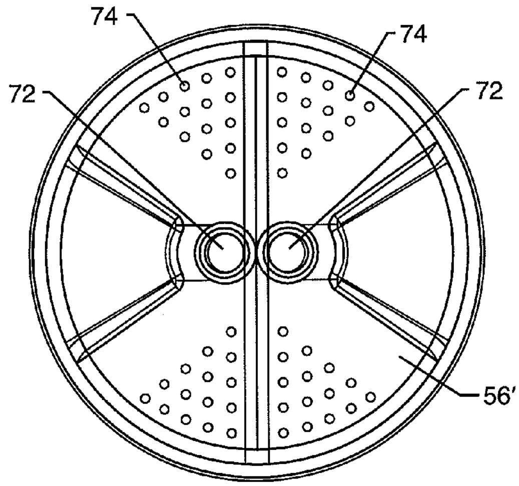
FIG. 8 is a to plan view similar to FIG. 5, but showing an alternative preferred form of the eyewash body to include a plurality of perforated ports for use as a combined eyewash/facewash unit.
Figure 9:
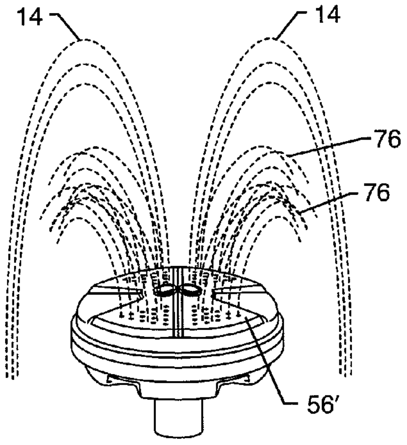
FIG. 9 is a simplified perspective view similar to FIG. 6, but showing a plurality of relative small facewash streams in combination the diverging eyewash flush streams directed upwardly from the modified eyewash body of FIG. 8.

FIGS. 8 and 9 illustrate one alternative preferred form of the invention, wherein a modified discharge plate 56' on the eyewash body 48 additionally includes a large plurality or large array of relatively small facewash ports 74 in addition to the pair of larger eyewash ports 72. When these small facewash ports 74 are included, the overall upward water flow from the eyewash body 48 includes the pair of diverging eyewash streams 14, in combination with a large plurality of smaller facewash streams 76 (FIG. 9) aimed to extend over and to drench a person's face with a flush flow of water to flush irritants or contaminants from the person's face. This modified discharge plate 56' mounts quickly and easily onto the lower base member 54 (not shown in FIGS. 8-9) of the eyewash body 48 to provide an interchangeable modular design.

Figure 10:
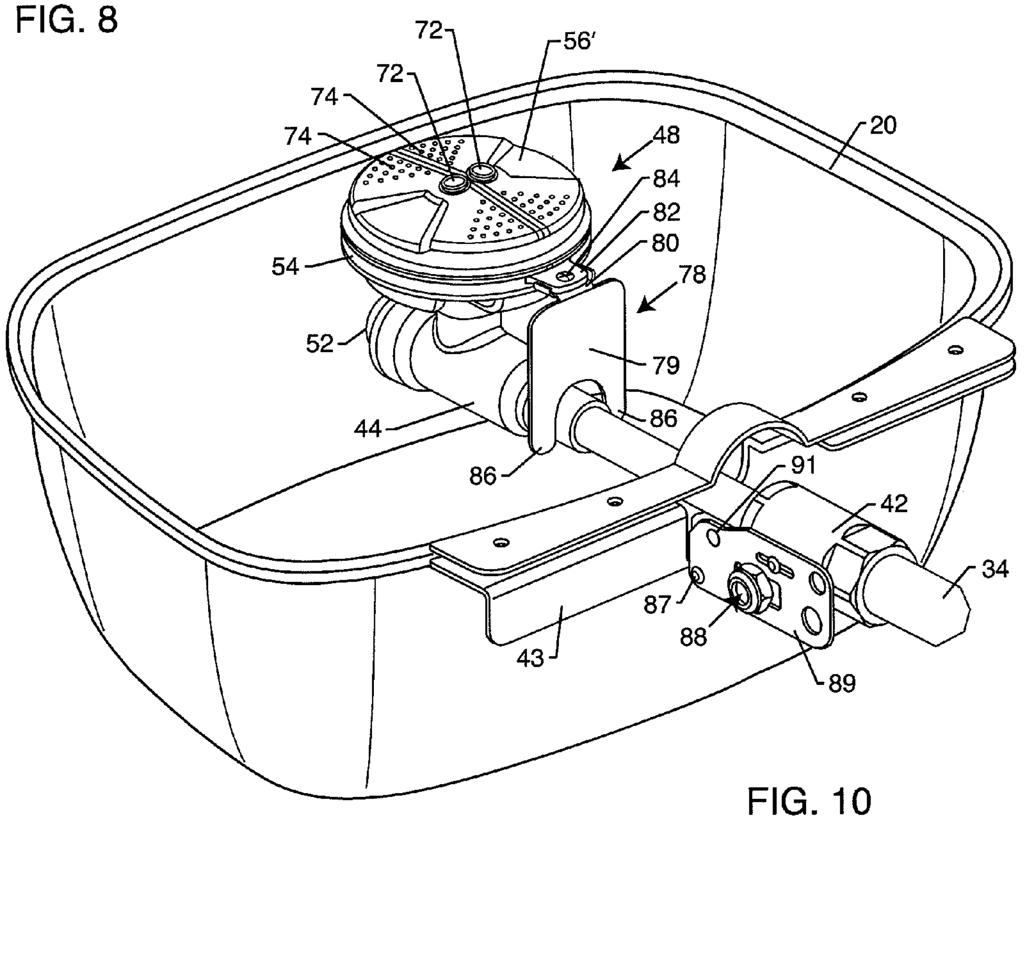
FIG. 10 is a top perspective view of the eyewash unit illustrating a lock clip for preventing rotational disassembly of the eyewash body from the unit.

FIG. 10 shows a lock clip 78 engaged between the installed eyewash body 48 and the L-strainer 44 for normally preventing undesired rotational disassembly of the eyewash body 48 from the elbow fitting. As shown, the lock clip 78 comprises a relatively simple plate-shaped device having an upper tang 80 turned generally horizontally for removable attachment to a small flange 82 on the eyewash body 48, as by means of threaded fastener 84. From the upper tang 80, the lock clip 78 defines a downwardly extending plate 79 which terminates in a pair of spaced-apart or forked lower legs 86. These lower legs 86 are dimensioned to fit with relatively close tolerance at opposite sides of the L-strainer 44, or alternately at opposite sides of the water supply conduit 34, when the lock clip 78 is attached to the eyewash body 48. With this construction, the depending legs 86 of the lock clip 78 effectively obstruct and thereby prevent rotational movement of the eyewash body 48 relative to the L-strainer 44, and thereby prevent undesired rotational disassembly of the eyewash body 48 unless and until the lock clip 78 is disconnected from the body flange 82. A tool (not shown) is required to remove the fastener 84 to achieve disassembly of the eyewash body 78 from the underlying L-strainer 44.

FIG. 10 additionally shows the valve housing 42 connected between the water supply conduit 34 and an upstream end of the L-strainer 44, wherein this valve housing 42 has a rotatable actuator 88 for opening and closing an internal valve (not shown) within the housing 42. The cover 38 is connected to this rotatable actuator 88 for shifting the valve (not shown) between the closed and open positions as the cover is moved respectively between the closed and open positions, as previously described herein. The hinge assembly 43 on the rear margin of the cover or lid 38 is connected by a screw 87 or the like to a bracket plate 89 forming part of the rotatable actuator 88. With this construction, normal raising and lowering of the cover 38 shifts the bracket plate 89 relative to the connector 42 for respectively opening and closing a valve (not shown) within the connector 42. However, upon removal of the screw 87, the cover 38 is rotatable relative to the bracket plate 89 via a pivot joint 91, whereby the cover 38 can be opened without turning on the water flow as may be desired, e.g., when flushing the filter screen 45 within the L-strainer 44.

Figure 11:
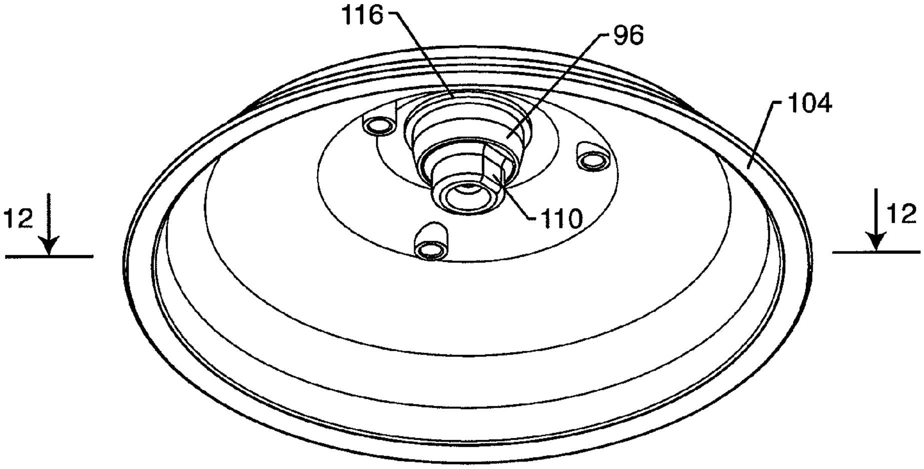
FIG. 11 is a bottom side perspective view of a shower head for use in the combined eyewash and emergency shower station of FIG. 1.
Figure 12:
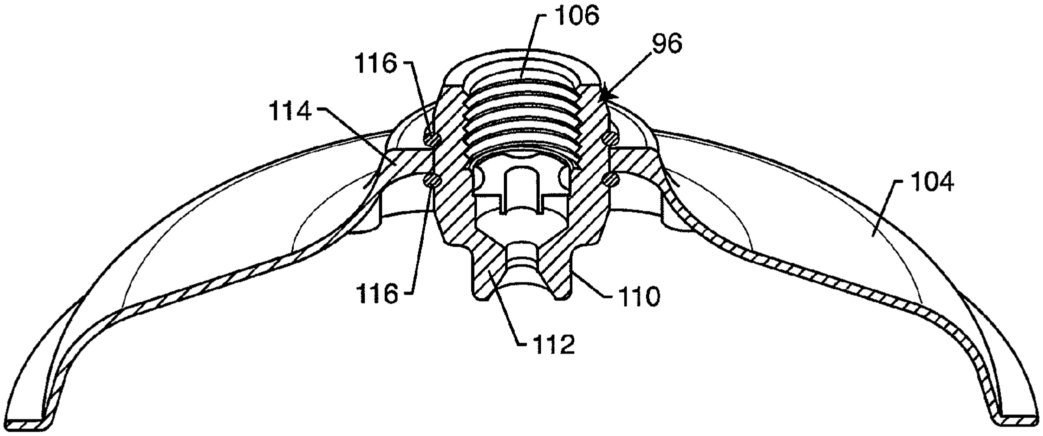
FIG. 12 is a vertical sectional view taken generally on the line 12-12 of FIG. 11.

FIGS. 11-12 illustrate a further adaptation of the invention, wherein an emergency shower station 90 (FIGS. 1,11 and 12) is included as part of the emergency wash station 10. As shown best in FIG. 1, the support stand 30 continues upwardly from the water supply tee fitting 35 to an upper elbow 92 whereat a second water supply conduit 94 extends generally horizontally to an emergency shower head 96 (FIGS. 11-12). A valve housing 98 is included along the conduit 94 and is adapted for quick and easy emergency opening, as by means of pull cord 100 and handle 102 (FIG. 1) for providing water under pressure to the shower head 96. The wash station 10 thus also accommodates, when needed, emergency shower wash-off of irritants or contaminants from a person.

FIGS. 11-12 show an improved subassembly including the emergency shower head 96 carrying a downwardly open, generally inverted bell-shaped shower shroud 104. In accordance with the invention, the shower head 96 comprises a compact body having a threaded upstream end 106 for quick and easy threaded connection with a downstream end of an elbow fitting 108 (FIG. 1) attached to the water supply conduit 94. Rotational mounting and/or rotational disassembly of the shower head 96 is achieved by means of a tool (not shown) engaging wrench flats 110 formed on a downstream nozzle portion 112 of the shower head body.

Importantly, the shroud 104 is carried on the shower head 96 in a manner permitting rotation shroud displacement relative to the shower head 96, without rotational disassembly of the shower head 96 from the associated conduit fitting 108. That is, as shown best in FIG. 12, the shroud 104 includes a central hub 114 which is rotatably carried about the body of the shower head 96 between a pair of retaining rings 116 which prevent any significant axial displacement of the shroud 104. Alternately, if desired, one of the retaining rings 116 can be substituted by other retaining means, such as a radially enlarged shoulder on the shower head body. With this construction, rotational displacement of the shroud 104 does not loosen or disassemble the shower head 96.

FIGS. 13-19 show a preferred construction for the shower head including the rotatable shroud 104. In this preferred form, the shower head includes a modified nozzle subassembly in the form of a nozzle body 96' having a plurality of flow control and stream shaping components mounted therein, wherein this modified combination is designed to provide a regulated outflow of shower water which is substantially constant over a range of normal water inflow pressures, and further wherein the produced shower stream is relatively uniformly dispersed throughout a defined generally cone-shaped shower spray pattern to insure thorough rinsing of contaminants from a person using the shower. In this regard, the modified shower head combination is designed for substantially complete compliance with applicable safety codes and standards.

Figure 13:
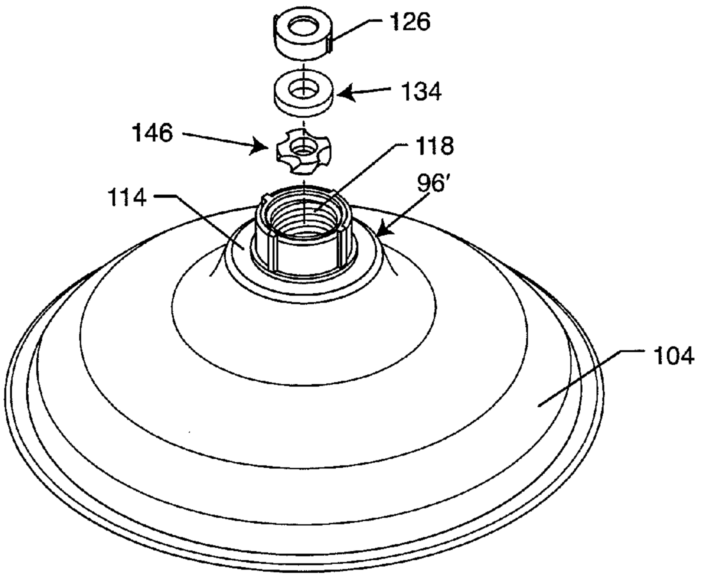
FIG. 13 is an exploded top perspective view of one preferred shower head construction included multiple flow control and stream shaping components mounted within a modified nozzle body.
Figure 14:
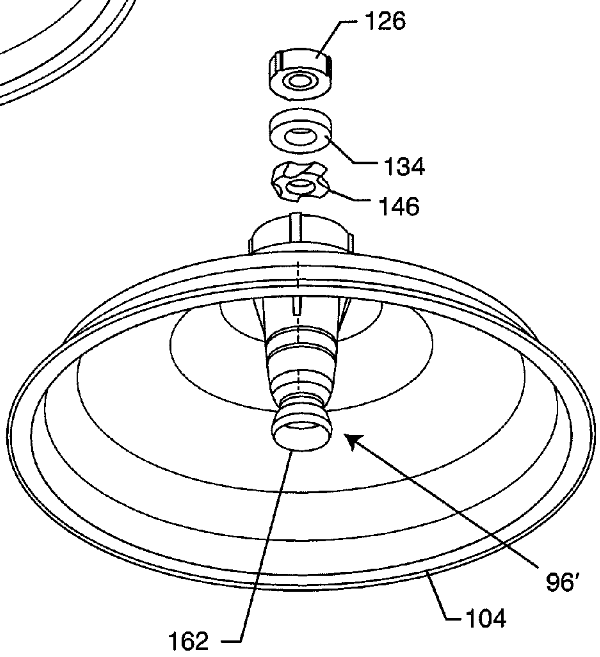
FIG. 14 is an exploded bottom perspective view of the shower head construction shown in FIG. 13.
Figure 15:
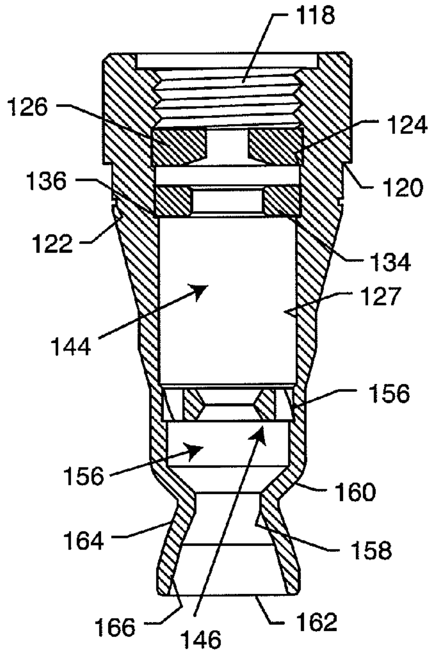
FIG. 15 is a vertical sectional view illustrating the nozzle body of FIGS. 13-14 with the multiple flow control and stream shaping components mounted therein.

More particularly, as viewed best in FIGS. 13-15, the modified nozzle body 96' comprises a unitary structure having an upstream end 118 that is internally threaded for threaded mounting onto the downstream end of the shower water supply conduit 94 (as viewed in FIG. 1), as by appropriate coupling to a downstream end of the elbow fitting 108 mounted onto the conduit 94. The outer surface of the modified nozzle body 96' includes a radially enlarged shoulder 120 for seating against an upper side of the hub 114 of the shroud 104, in combination with a ring groove 122 (FIG. 15) in axially spaced related to said shoulder 120 for receiving a retaining ring 116 (FIG. 12) for supporting the shroud 104 on the nozzle body 96' while permitting relatively free rotation between the shroud 104 and the nozzle body 96'.

The interior of the modified nozzle body 96' includes a number of stepped shoulders formed therein to define mounting stops for each of the multiple flow control and stream shaping components to be mounted therein. Specifically, an upper shoulder 124 is formed generally at the downstream end of the internally threaded end 118. This upper shoulder 124 defines a stop for seated support of a flexible pressure compensating flow control element 126. This flow control element 126, shown in more detail in FIG. 16, comprises a resilient or flexible ring mounted along a central flow path 127 through the nozzle body 96', and defines a central flow control port 128. External tabs (not shown) may be provided on the periphery of the flow control element 126 to assist in locating and retaining the element 126 relative to the threaded end 118 of the nozzle body 96'.

Figure 16:
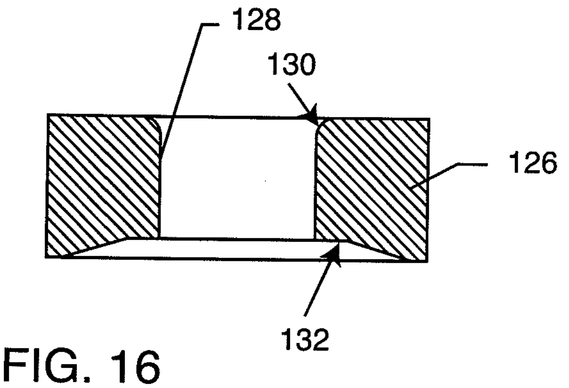
FIG. 16 is an enlarged vertical sectional view of a pressure compensating flexible flow control element for mounting into the nozzle body of FIGS. 13-15.

As is known in the art, the flow control port 128 is designed for regulating the rate of water flow through the element 126 to a substantially constant water outflow in response to a range of different upstream water supply pressures. In the illustrative embodiment, the flow control element 126 is designed to maintain a substantially constant water outflow of at least about 20 gallons per minute in response to water supply pressures within a normal pressure range of about 30 to about 90 psi. As shown in FIG. 16, a preferred flow control element 126 defines the flow control port 128 with a beveled or smoothly radiused upstream edge (arrow 130), in combination with an axially inset downstream margin (arrow 132). With this geometry, the flow control port 128 is able to effectively shift in diametric size to achieve the desired substantially constant water outflow rate. In an unstressed state, a preferred diametric size is about 0.438 inch, and a preferred axial thickness is about 0.4 inch.

The flow control element 126 is, in the preferred form as shown best in FIG. 15, spaced a short distance axially upstream from a flow control positioning spacer or washer 134. However, persons skilled in the art will recognize and appreciate that the axially inset downstream margin 132 circumscribing the flow control port 128 permits proper regulatory operation by the flow control element 126 in the event that this axial spacing is eliminated.

Figure 17:
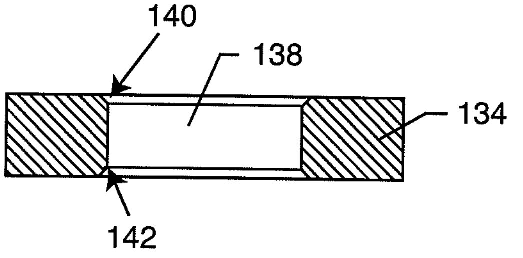
FIG. 17 is an enlarged vertical sectional view of a flow control positioning washer for mounting into the nozzle body of FIGS. 13-15.
Figure 18:
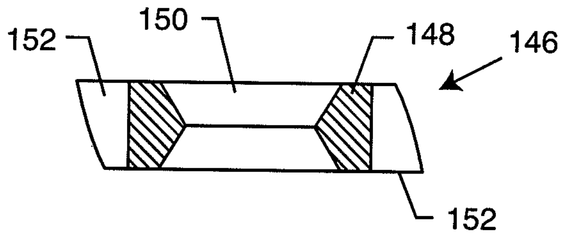
FIG. 18 is an enlarged vertical sectional view of a diffuser disk for mounting into the nozzle body of FIGS. 13-15.
Figure 19:
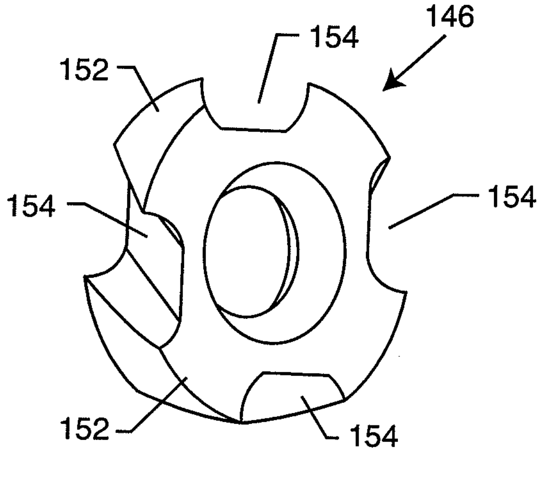
FIG. 19 is a perspective view of the diffuser disk of FIG. 18.

The flow control spacer washer 134 comprises a relatively sturdy, or substantially non-flexible or rigid component seated within the nozzle body 96' against a second, slightly smaller diameter internal step shoulder 136. The spacer washer 134 (shown best in FIG. 17) defines a central flow port 138 having a diametric size that is larger than the size of the flow control port 128 formed in the flow control element 126. In a preferred form, the diametric size of the central flow port 138 in the spacer washer 136 is about 0.530 inch, whereas the diametric size of the preferred flow control port 128 in the element 126 is about 0.438 inch. The spacer washer 136 functions by substantially reducing turbulent flow while converting the water passing therethrough to a substantially unified or columnar stream approaching laminar flow characteristics. Such reduced turbulence is enhanced by increasing the thickness of the spacer washer, with a washer thickness of about 0.235 inch in the preferred form, and by smoothly beveling the upstream and downstream edges of the central flow port 138 (as indicated in FIG. 17 by arrows 140 and 142, respectively).

From the flow control spacer washer 134, the discharged water stream passes into an axially elongated first mixing chamber 144 (FIG. 15) located between the washer 134 and a diffuser disk 146. The diffuser disk is shown in more detail in FIGS. 18-19. As shown, the diffuser disk 146 comprises an annular ring 148 defining a flow port 150 having conically tapered upstream and downstream ends, in combination with a plurality of outwardly radiating swirl vanes 152 set angularly to define a corresponding plurality of angled swirl passages 154. The outer peripheries of these vanes 152 are sized to rest and seat upon a third and slightly smaller diameter internally stepped shoulder 156 formed within the nozzle body 96'. In the preferred form as shown, there are four swirl vanes 152 each set at an angle of about 45 to an axial centerline of the nozzle body 96'. In addition, the diametric size of the flow port 150 in the diffuser disk 146 is less than the diametric size of the central flow port 138 in the spacer washer 134, with a preferred diffuser disk flow port size being about 0.362 inch. In addition, the radial sizes of the swirl passages 154 are selected to provide the desired final shower spray pattern (as will be described in more detail), with the illustrative swirl passages 154 each being formed with a radial dimension of about 0.337 inch.

In operation, water discharged through the spacer washer 134 substantially in the form of a unified stream. At least a portion of this water stream impacts the annular ring 148 of the diffuser disk 146, thereby creating turbulence at the upstream side of the diffuser disk. The result is that a portion of the water discharged through the spacer washer 134 passes axially through the diffuser disk flow port 150, and another portion of this water passes with a spinning or swirling action through the swirl passages 154 defined between the angularly set swirl vanes 152. In this regard, the axial length of the first mixing chamber 144 is sufficiently long, preferably at least about equal to the mixing chamber diametric size, with the illustrative drawings showing a mixing chamber length of at least about 1.0 inch, and more preferably about 1.3 inches.

The combined water flow passing through the diffuser disk 146 enters a second mixing chamber 156 defining a short axial spacing between the diffuser disk 146 and a nozzle orifice 158 formed in the nozzle body 96'. As shown in FIG. 15, the nozzle orifice 158 has a diametric size greater than the size of the central flow port 150 in the diffuser disk 146 to align generally axially with the annular ring 148 of the diffuser disk. A preferred size for the nozzle orifice 158 is about 0.5 inch. This size, in combination with inwardly angled walls 160 on the nozzle body 96' defining a downstream segment of the second mixing chamber 156 causes further mixing of the stream-like water passing through the flow port 150 of the diffuser disk 146 with the swirling outer water flows passing through the swirl passages 154.

The water discharged from the nozzle orifice 158 flows into a conically expanding exit cone 162 which permits the swirling water portion to expand by centrifugal action radially outwardly within the limits of the exit cone geometry. Importantly, this creates a substantially uniform water distribution or dispersion over the entire volume discharged from the nozzle body 96' for effective washing of contaminants from a person using the shower. In the preferred form, to reduce the overall size of the exit cone 162 which additionally confining the shower spray pattern for compliance with safety codes and standards, the exit cone 162 in the preferred form defines a first cone segment 164 angling outwardly from the nozzle orifice 158 at an included angle of about 45 relative to an axial centerline of the nozzle body 96', and then merging with a second cone segment 166 angling outwardly at an included angle of about 30 from said centerline. Alternately, a curved surface may be used in lieu of the two relatively straight conical segments.

A variety of further modifications and improvements in and to the emergency wash station of the present invention will be apparent to persons skilled in the art. By way of example, the emergency wash station 10 may be constructed to include only the eyewash unit 12, or the combined eyewash/facewash unit, and/or additionally include the emergency shower unit 90. In the eyewash and/or combined eyewash/facewash configurations, the unit can be adapted for pole mounting as shown, or alternately for pedestal or wall mounting as known by persons skilled in the art. Or, if desired, the unit may be incorporated into a portable or gravity feed eyewash unit such as the type shown in U.S. Pat. No. D529,185, which is incorporated by reference herein. In addition, if desired, the components of the eyewash body 48 can be constructed from a lightweight molded plastic which may incorporate an antimicrobial substance. Accordingly, no limitation on the invention is intended by way of the foregoing description and accompanying drawings, except as set forth in the appended claims.

What is claimed is:

1. A method for flushing contaminants from a person's eyes, the method comprising:

causing a first stream of water to flow from a first discharge port included in an eyewash unit and simultaneously causing a second stream of water to flow from a second discharge port included in the eyewash unit; and causing the first and second streams of water to arch upwardly and diverge angularly from each other, thereby causing the first and second streams of water to flow laterally from the insides of a person's eyes when the person leans over the first and second streams of water to the outsides of the person's eyes.

2. The method of claim 1, wherein causing the first and second streams of water to flow from the first and second discharge ports, respectively, includes generating streams that are relatively solid and have substantially laminar flow.

3. The method of claim 1, wherein the first and second discharge ports are formed in a discharge plate of the eyewash unit.

4. The method of claim 1, wherein causing the first and second streams to diverge angularly from each other is accomplished by:

forming the first discharge port to include a first bore defining a first longitudinal axis;

forming the second discharge port to include a second bore defining a second longitudinal axis; and forming the first and second bores such that the first and second longitudinal axes intersect to form an acute angle.

5. The method of claim 1, wherein causing the first and second streams to diverge angularly from each other is accomplished by:

forming the first discharge port to include a first bore defining a first longitudinal axis;

forming the second discharge port to include a second bore defining a second longitudinal axis; and forming the first and second bores such that the first and second longitudinal axes are disposed along a substantially vertical plane.

6. The method of claim 1, further comprising:

causing a shower stream of water to flow downward from a shower head.

7. The method of claim 1, further comprising:

causing a plurality of relatively small facewash streams of water to flow from the eyewash unit to flush contaminants from the person's face.

8. The method of claim 1, further comprising:

activating an activation handle of a valve in the eyewash unit; and causing the first and second streams of water to start flowing in response to activation of the activation handle.

9. The method of claim 1, further comprising:

opening a cover mounted to the eyewash unit, the cover provided for concealing the first and second discharge ports from users when the cover is in a closed position and exposing the first and second discharge ports when the cover is in an open position; and causing the first and second streams of water to start flowing in response to opening of the cover.

10. A method for flushing a person's eyes, the method comprising:

opening a valve connected to a liquid supply conduit;

causing a first stream of water to flow from a first discharge port included in an eyewash unit and simultaneously causing a second stream of water to flow from a second discharge port included in the eyewash unit;

causing the first and second streams of water to arch upwardly and diverge angularly from each other;

placing one's eyes in the first and second streams of water; and flushing contaminants in the eyes in a direction substantially away from the lacrimal punctum toward the excretory lacrimal ducts.

11. The method of claim 10, wherein causing the first and second streams of water to flow from the first and second discharge ports, respectively, includes generating streams that are relatively solid and have substantially laminar flow.

12. The method of claim 10, wherein the first and second discharge ports are formed in a discharge plate of the eyewash unit.

13. The method of claim 10, wherein causing the first and second streams to diverge angularly from each other is accomplished by:

forming the first discharge port to include a first bore defining a first longitudinal axis;

forming the second discharge port to include a second bore defining a second longitudinal axis; and forming the first and second bores such that the first and second longitudinal axes intersect to form an acute angle.

14. The method of claim 10, wherein causing the first and second streams to diverge angularly from each other is accomplished by:

forming the first discharge port to include a first bore defining a first longitudinal axis;

forming the second discharge port to include a second bore defining a second longitudinal axis; and forming the first and second bores such that the first and second longitudinal axes are disposed along a substantially vertical plane.

15. A method for flushing a person's eyes using an emergency eyewash unit, the method comprising:

projecting a first eyewash discharge stream that arches upwardly and outwardly in a first plane and simultaneously projecting a second eyewash discharge stream that arches upwardly and outwardly in a second plane;

projecting the first and second eyewash discharge streams such that the first and second planes are substantially coplanar; and causing the first and second eyewash discharge streams to diverge angularly from each other.

16. The method of claim 15, wherein projecting the first and second eyewash discharge streams includes generating streams that are relatively solid and have substantially laminar flow.

17. The method of claim 15, further comprising:

causing the first and second eyewash discharge streams to flow laterally from the insides of a persons' eyes to the outsides of the person's eyes when the person leans over the first and second eyewash discharge streams.

18. The method of claim 15, further comprising:

causing the first and second eyewash discharge streams to flow laterally substantially from the lacrimal punctum of a person's eyes to the excretory lacrimal ducts of the person's eyes when the person places his eyes in the first and second eyewash discharge streams.

19. The method of claim 15, wherein causing the first and second eyewash discharge streams to diverge angularly from each other is accomplished by:

forming a first discharge port in an eyewash body of the eyewash unit, the first discharge port including a first bore defining a first longitudinal axis;

forming a second discharge port in the eyewash body of the eyewash unit, the second discharge port including a second bore defining a second longitudinal axis;

forming the first and second bores such that the first and second longitudinal axes intersect to form an acute angle; and projecting the first and second eyewash discharge streams from the first and second discharge ports, respectively.

20. The method of claim 15, wherein causing the first and second eyewash discharge streams to diverge angularly from each other is accomplished by:

forming a first discharge port in an eyewash body of the eyewash unit, the first discharge port including a first bore defining a first centerline;

forming a second discharge port in the eyewash body of the eyewash unit, the second discharge port including a second bore defining a second centerline;

forming the first and second bores such that the first and second centerlines are disposed along a substantially vertical plane; and projecting the first and second eyewash discharge streams from the first and second discharge ports, respectively.

* * * * *